United States Patent [19]
Takahashi et al.

[11] Patent Number: 5,616,691
[45] Date of Patent: Apr. 1, 1997

[54] PROCESS FOR PRODUCING ALBUMIN PREPARATION

[75] Inventors: Tuyoshi Takahashi; Kazuo Ikegaya; Shinobu Mochizuki; Hideo Nishimaki, all of Osaka, Japan

[73] Assignee: The Green Cross Corporation, Osaka, Japan

[21] Appl. No.: 456,484

[22] Filed: Jun. 1, 1995

[30] Foreign Application Priority Data

Jun. 1, 1994 [JP] Japan .................. 6-119977

[51] Int. Cl.$^6$ .......................... C07K 3/22
[52] U.S. Cl. .................. 530/364; 530/416; 530/417; 210/263; 210/290; 210/660; 210/661; 210/663; 210/679
[58] Field of Search .................. 530/362, 363, 530/364, 416, 417; 436/88; 210/660, 661, 663, 679, 263, 290; 514/21

[56] References Cited

U.S. PATENT DOCUMENTS

| | | |
|---|---|---|
| 4,043,997 | 8/1977 | Schroeder . |
| 4,075,197 | 2/1978 | Schuck et al. . |
| 4,086,222 | 4/1978 | Lindquist et al. ............ 530/364 |
| 4,228,154 | 10/1980 | Fisher et al. . |
| 5,277,818 | 1/1994 | Matsuoka et al. . |

FOREIGN PATENT DOCUMENTS

| | | |
|---|---|---|
| 0121468A3 | 3/1984 | European Pat. Off. . |
| 0367220A2 | 10/1989 | European Pat. Off. . |
| 0428758A1 | 6/1990 | European Pat. Off. . |
| 0559895A1 | 11/1991 | European Pat. Off. . |
| 0570916 | 11/1993 | European Pat. Off. . |
| 0144714 | 9/1994 | European Pat. Off. . |
| 2327256 | 10/1976 | France . |
| 2537123 | 3/1977 | Germany . |

OTHER PUBLICATIONS

*Purification Chromatograhique de l'albumine plastique humaine a l'echelle pilote*, 1987, pp. 103–106.
9–Biochem Methods, vol. 108, 1988, pp. 283 Abstract 108:218559j.

*Primary Examiner*—Nathan M. Nutter
*Attorney, Agent, or Firm*—Sughrue, Mion, Zinn, Macpeak & Seas

[57] ABSTRACT

The process for producing the albumin preparation of the present invention comprises treating an aqueous albumin solution with an anion exchanger and a cation exchanger and subjecting the solution to heat treatment wherein a polyacrylamide type carrier having a cation exchange group is used as a cation exchanger. By using a polyacrylamide type carrier as a cation exchanger, the polymerization caused by the contaminating proteins can be suppressed, and a highly purified albumin preparation can be obtained.

13 Claims, No Drawings

PROCESS FOR PRODUCING ALBUMIN PREPARATION

FIELD OF THE INVENTION

The present invention relates to a process for producing an albumin preparation.

BACKGROUND OF THE INVENTION

Serum albumin, the protein found in the highest concentration in serum, maintains the osmotic pressure of blood and transports nutritive substances or metabolites bound thereto. A preparation containing the above-mentioned serum albumin is used in the treatment of, for example, hypoalbuminemia caused by the loss of albumin, dysfunction of albumin synthesis and hemorrhagic shock. An albumin preparation in the form of an aqueous solution is heat-treated in order to inactivate viruses which might contaminate the preparation.

The results of gel filtration analysis of a commercially available albumin preparation produced by the above-mentioned method indicate that aggregates were present in said preparation. The aggregates (which are commonly called "polymers" and thus are hereinafter referred to as such) are rarely observed before the above-mentioned heat treatment. Thus, it can be inferred that albumin becomes aggregated upon the heat treatment possibly due to the action of contaminating proteins which are unstable to heat. Since commercially available albumin preparations have been widely and safely used, it is believed that these polymers are harmless to humans. However, it is preferable to minimize the content of polymers in albumin solutions, since the polymers are heat denaturation products.

Further, albumin contains contaminating proteins such as transferrin, the physicochemical properties of which are relatively similar to those of albumin. Since it is difficult to efficiently separate these contaminating proteins from albumin by conventional methods such as fractionation, there is the problem of contamination of an albumin preparation by these proteins.

Various purification methods for preparing serum albumin preparations utilizing ion exchangers are known. That is, a method exists comprising an anion exchanger treatment at a pH in the range of 4.5 to 4.9 followed by a cation exchanger treatment at a pH in the range of 5.2 to 6.5 (U.S. Pat. No. 4,086,222 and FR 2327256), a method exists comprising three steps which comprise a hydrophilic anion exchanger treatment, a hydrophobic anion exchanger treatment and a hydrophilic cation exchanger treatment wherein the hydrophilic cation exchanger is CM-Trisacryl (U.S. Pat. No. 4,675,384 and EP 121468), a method exists which comprises treating an aqueous solution containing serum albumin with an anion exchanger at pH 5.1 to 5.5 for removing a polymer-forming factor present in the solution (U.S. Pat. No. 5,277,818 and EP 367220), and a method exists which comprises treating an aqueous solution containing serum albumin with an anion exchanger and then with a cation exchanger, and subjecting the solution to heat treatment (EP 428758), a method exists which further comprises preserving the aqueous solution containing serum albumin prepared by above-mentioned methods, in a dealkalized soft glass container for keeping the alminium content very low (U.S. Pat. No. 5,372,997 and EP 559895), and a method exists which comprises treating an aqueous solution containing serum albumin with an anion exchanger such as QMA-Sepharosil at pH 4.7 (Bio-Science, Vol. 6, No. 4, p. 103–106 (1987)).

An object of the present invention is to provide a process for producing an albumin preparation which makes it possible to highly purify an albumin, to reduce the content of contaminating proteins, including transferrin, and to lower formation of polymers after heat treatment than the detectable limit as described herein, by improving the purification steps of albumin.

SUMMARY OF THE INVENTION

As a result of extensive studies, the present inventors found that the above-described problems could be solved by using a polyacrylamide type carrier as a cation exchanger during the cation exchanger treatment.

The present invention is directed to a process for producing an albumin preparation which comprises treating an aqueous solution containing serum albumin with an anion exchanger and then with a cation exchanger, and subjecting the solution to heat treatment, wherein said cation exchanger is a polyacrylamide type carrier having a cation exchange group.

DETAILED DESCRIPTION OF THE INVENTION

The origin of the albumin which is the starting material in the production process of the present invention is not particularly restricted. Examples thereof include those albumins originating from mammals such as human, bovine and rabbit. In particular, human albumin may be used. As an example of a starting material from which the albumin is to be prepared, the fraction V obtained by Cohn's cold alcoholic fractionation may be used.

The albumin preparation of the present invention may be obtained by dissolving the above-described serum albumin fraction V in an appropriate purified water and treating the albumin-containing aqueous solution thus obtained with an anion exchanger and then with a cation exchanger followed by heat treatment. In the above-described process, the albumin content of the albumin-containing aqueous solution may be adjusted to approximately 0.1 to 30% (W/V, the same will apply hereinafter unless otherwise noted) and preferably to approximately 1 to 10%.

According to the present invention, the aqueous albumin solution is first purified by treating with an anion exchanger. Contaminating proteins having an isoelectric point lower than that of albumin, such as haptoglobin and $\alpha_1$-acidic glycoprotein, are removed. As the usable anion exchanger, any inert carrier may be used so long as it has an anion exchange group. Specific examples of anion exchange groups include diethylaminoethyl groups (commonly called DEAE), quaternary ammonium groups such as diethy[2-hydroxypropyl]aminoethyl groups (commonly called QAE), $(CH_3)_3N^{30}CH_2$—(commonly called Q), quaternary methylammonium groups (QMA) and the like. Specific examples of inert carriers include dextran (Sephadex 200 manufactured by Pharmacia), agarose (Sepharose ® manufactured by Pharmacia), vinyl hydrophilic polymers (Toyopearl® manufactured by Tosoh corporation), cellulose (Cellulofine® manufactured by Seikagaku Corporation), porous silica gel (Sepharosil® manufactured by SEPRACOR) and the like. Specific examples thereof include anion exchangers commonly used in the art, for example, DEAE-Sepharose® and Q-Sepharose®(each manufactured by Pharmacia), DEAE-Toyopearl® and QAE-Toyopearl®(each manufactured by Tosoh corporation), A® Cellulofine® (manufactured by Seikagaku Corporation), QMA-Sepharosil®

(manufactured by SEPRACOR), anion exchange resins and the like. From the viewpoint of the efficiency of the removal of contaminating proteins, it is preferable to use a strongly basic anion exchanger such as Q-Sepharose, QAE-Toyopearl or QMA-Sepharosil.

The above treatment with an anion exchanger may be performed by contacting the aqueous albumin solution with the anion exchanger. The amount of the anion exchanger may be appropriately adjusted, depending on the content of the contaminating proteins in the albumin-containing aqueous solution and the performance of the anion exchanger, to about 0.1 to 5 ml, preferably to about 3 ml, of the anion exchanger per gram of albumin is used. This treatment may be performed either by a column method or by a batch method. The column method is preferred from the viewpoint of the efficiency of removal of the contaminating proteins.

When the treatment is to be performed by the column method, the pH value of the above-mentioned aqueous albumin solution is adjusted to about 3 to 6, preferably to about 4.5 to 5.5, more preferably to about 5.1 to 5.4, and the salt concentration thereof is adjusted to about 0.001 to 0.2 M, in terms of sodium chloride, preferably to about 0.001 to 0.05 M. Then, the resulting aqueous solution is passed through an anion exchanger column which has been equilibrated with a buffer solution, for example, a 0.02 M sodium acetate buffer (pH 5.1), and then developed with said buffer solution to recover the unabsorbed fraction. To suppress the denaturation of albumin, the above procedure is preferably performed at a low temperature (i.e., usually 10° C. or below). When the treatment is to be performed by the batch method, an anion exchanger is added to the aqueous albumin solution, which has been adjusted to the conditions as specified above, to thereby contact these materials. After stirring at a temperature of 10° C. or below for 30 minutes to 2 hours, the aqueous solution is separated from the anion exchanger by, for example, centrifugation, and the supernatant is recovered.

The pH value and concentration of the aqueous albumin solution thus purified by the above anion exchanger treatment is adjusted, if required. Then, it is further purified by treating with a cation exchanger. This cation exchanger treatment makes it possible to remove contaminating proteins such as transferrin having an isoelectric point higher than that of albumin. As the cation exchanger, any polyacrylamide type carrier may be used so long as it has a cation exchange group. Examples of a suitable cation exchange group include a sulfo group such as sulfopropyl group (commonly called SP) or a carboxyl group such as a carboxymethyl group (commonly called CM). A polyacrylamide type carrier is an insoluble carrier consisting of a polymer of (metha)acrylamide, for example, poly(N-tris[hydroxymethyl]methylmethacrylamide) (Trisacryl® manufactured by SEPRACOR) and the like. From the viewpoint of the efficiency of the removal of contaminating proteins, it is preferable to use a cation exchanger such as sulfopropyl type polyacrylamide (SP-Trisacryl® manufactured by SEPRACOR), carboxymethyl type polyacrylamide (CM-Trisacryl® manufactured by SEPRACOR) and the like.

The above treatment with a cation exchanger may be performed by contacting the aqueous albumin solution purified by the above-mentioned anion exchanger treatment with the cation exchanger. The amount of the cation exchanger may be appropriately adjusted, depending on the content of the contaminating proteins in the albumin-containing aqueous solution and the performance of the cation exchanger, to about 0.1 to 5 ml, preferably to about 2 ml, of the cation exchanger per gram of albumin. This treatment may be performed either by a column method or by a batch method. However, the column method is preferred from the viewpoint of the efficiency of the removal of the contaminating proteins.

When the treatment is to be performed by the column method, the pH value of the above-mentioned aqueous albumin solution is adjusted to about 4 to 8, preferably to about 4.5 to 6.5, more preferably to about 5.0 to 6.0, and the salt concentration thereof is adjusted to about 0.001 to 0.2 M, in terms of sodium chloride, preferably to about 0.001 to 0.05 M. Then, the aqueous solution is passed through a cation exchanger column which has been equilibrated with a buffer solution (for example, a 0.02 M sodium acetate buffer (pH 5.5)) and then developed with said buffer solution to recover the unabsorbed fraction. To suppress the denaturation of albumin, the above procedure is preferably performed at a low temperature (i.e., usually 10° C. or below). When the treatment is to be performed by the batch method, a cation exchanger is added to the aqueous albumin solution, which has been adjusted to the conditions as specified above, to thereby contact these materials. After stirring at a temperature 10° C. or below for 30 minutes to 2 hours, the aqueous solution is separated from the cation exchanger by, for example, centrifugation and the supernatant is recovered.

With respect to the content of contaminating proteins contained in the aqueous albumin solution thus purified by the treatments with the anion exchanger and cation exchanger, the amount of haptoglobin, transferrin and $\alpha_1$-acidic glycoprotein each is lower than the detectable amount, which indicates that the albumin preparation contains little contaminating protein.

The concentration of the aqueous albumin solution, in which the content of contaminating proteins have been reduced by the above-described treatments with the anion exchanger and the cation exchanger, is adjusted to an appropriate level, and the resulting solution is formulated into a preparation of desired form, for example, filled into an ampule, and then subjected to heat treatment. The albumin preparation of the present invention thus is obtained. The above heat treatment, which aims at inactivating viruses which might contaminate the albumin preparation, is performed in the form of an aqueous solution having an albumin concentration of about 5 to 30%, preferably 5%, or 20 to 25%. The treatment may be performed at a temperature for a period of time sufficient for inactivating the contaminating viruses. For example, it may be performed at approximately 50° to 80° C., preferably at approximately 60° C., for approximately 5 to 20 hours, preferably for approximately 10 hours. Upon the above heat treatment, one or more stabilizers for albumin, for example, N-acetyltryptophan sodium or sodium caprylate, may be added, if required. These albumin stabilizers may be used at a rate of from about 20 to 60 mg, preferably about 40 mg, per gram of the albumin contained in the preparation.

The albumin preparation thus obtained shows substantially no polymer content (for example, the polymer content determined by gel filtration was lower than 0.5 wt% based on the albumin content) and substantially no transferrin content (for example, the transferrin content determined by single immunodiffusion was lower than 0.0056 wt% based on the albumin content). The albumin preparation of the present invention may be used in the same manner and in the same dose as those selected for conventional ones.

The present invention is illustrated further by way of the following non-limiting examples.

EXAMPLE 1

(a) Preparation of aqueous albumin solution

A paste of the fraction V (500 g) obtained by Cohn's cold alcoholic fractionation was dissolved in 2.0 liters of cold aseptic distilled water, and the pH value was adjusted to 4.6 with acetic acid, followed by stirring for approximately 1 hour. Then, the solution was filtered (filter: 0.45 μm) at approximately $-2°$ C., and then 2.0 liters of cold aseptic distilled water was further added. The pH value thereof was adjusted to 5.1 with 1 N sodium hydroxide to give an aqueous albumin solution.

(b) Treatment with anion

A column (diameter 8 cm× length 15 cm) was packed with QAE-Toyopearl (500 ml) and thoroughly washed with 0.5 M sodium chloride. Then, it was equilibrated with 0.02 M sodium acetate (pH 5.1) to give an anion exchanger column. The aqueous albumin solution obtained in the above treatment (a) was loaded onto the column which was then washed with cold 0.02 M sodium acetate (pH 5.1, 2 liters). The pass-through liquor was combined with the wash liquor, and the pH value thereof was adjusted to 5.5 with 1N sodium hydroxide.

(c) Treatment with cation exchanger

A column was packed with CM-Trisacryl (100 ml) and was washed thoroughly with 0.5 M sodium chloride. Then, it was equilibrated with 0.02 M sodium acetate (pH 5.5) to give a cation exchanger column. The aqueous albumin solution obtained in the above treatment (b) was passed over the column which was then washed with 0.02 M sodium acetate (pH 5.5, 0.5 liters). The pass-through liquor was combined with the wash liquor. The mixture was dialyzed and then concentrated with Pellicon to achieve an absorbance $A_{280}$ of 163 (albumin concentration: 28%).

(d) Heat treatment

An aqueous solution of stabilizers (containing 5.01 g of sodium N-acetyltryptophan and 3.10 g of sodium caprylate in 100 ml of said solution) was added to the aqueous albumin solution obtained in the above treatment (c) at a ratio of 1.2 ml per 10 ml of said aqueous albumin solution. The pH value of the mixture was adjusted to 6.85 with 1 N sodium hydroxide. Then, the albumin concentration was adjusted to 25% followed by aseptic filtration and an aliquot of the solution were pipetted into vials. After heat treatment at 60° C. for 10 hours, an albumin preparation was obtained.

Comparative Example

An albumin preparation was prepared in the same manner as in Example 1 except that SP-Toyopearl was used in place of CM-Trisacryl in the cation exchanger treatment step (c).

Experimental Example 1

(i) Examination of polymer content in albumin preparation

Each albumin preparation obtained in Example 1 and the Comparative Example was examined for polymer content by gel filtration. The gel filtration analysis was performed under the following conditions.

(a) Sample: The preparation of Example 1 and the preparation of Comparative Example were diluted 50-fold with the buffer solution as specified below and filtered (filter: 0.45 μm). Then, 20 μl of each solution was poured.

(b) Column: A column (diameter 7.8 mm× length 30 cm) packed with TSKgelG3000SW (manufactured by Tosoh Corporation) was used.

(c) Buffer solution: 0.1 M $KH_2PO_4$/0.3 M NaCl (pH 6.9).

(d) Flow rate: 1 ml/minute.

(e) Detection wavelength: $\lambda=280$ nm.

(f) Apparatus: Waters HPLC system.

Results of the examination are shown in Table 1. Both dimer content and polymer content of the preparation obtained in Example 1 were lower than that of the preparation obtained in Comparative Example which involved a conventional method. The polymer content of the preparation obtained in Example 1 was small, such as lower than 0.5 wt%, which indicates that the preparation contained little polymer.

(ii) Determination of contaminating protein content in albumin preparation

The content of $\alpha_1$-acidic glycoprotein ($\alpha_1$-AG), haptoglobin (Hp) and transferrin (Tf) in the preparations obtained by Example 1 and Comparative Example were determined. Table 1 shows the results. The contaminating protein content was determined by the single immunodiffusion method [Mancini's method: Mancini G. et al., Immunochemistry, Vol. 2, No. 3,235–254 (1965)]. The anti–$\alpha_1$ acidic glycoprotein serum, antihaptoglobin serum and antitransferrin serum employed in the tests were each prepared in rabbits as an immune animal by a conventional method. Standard curves of sedimentation area respectively corresponding to the contaminating proteins were prepared by using single immunodiffusion gels prepared from these antisera. According to the standard curves, the detectable limit of α-AG was 0.4 mg/dl, that of Hp was 1.6 mg/dl and that of Tf was 1.4 mg/dl. As shown in Table 1, the contents of α-Ag, Hp and Tf in the albumin preparation of the present invention were each lower than the detectable limit, which indicates that the albumin preparation contains little contaminating protein. As described above, the detectable limit of Tf was 1.4 mg/dl and an albumin content of the preparation of Example 1 was 25%. Therefore, the Tf content was lower than 0.0056 wt% based on the albumin content.

TABLE 1

| | | Example 1 | Comparative Example |
|---|---|---|---|
| Albumin | monomer | 98.7 wt % | 98.5 wt % |
| | dimer | 0.9 wt % | 1.0 wt % |
| | polymer | 0.4 wt % | 0.5 wt % |
| Content of contaminating protein based on 25% albumin concentration | $\alpha_1$-AG | <DL (0.4 mg/dl) | <DL (0.4 mg/dl) |
| | Hp | <DL (1.6 mg/dl) | 5.2 mg/dl |
| | Tf | <DL (1.4 mg/dl) | 1.5 mg/dl |

In the above Table 1, "<DL" means lower than the detectable limit.

EXAMPLE 2

An albumin preparation was prepared in the same manner as in Example 1 except that SP-Trisacryl was used in place of CM-Trisacryl in the cation exchanger treatment step (c). The polymer content and contaminating protein content of the albumin preparation thus obtained were examined in the same manner as in Experimental Example 1. As a result, the polymer content was lower than the detectable limit, and the Hp, $\alpha_1$-AG and Tf content were each lower than the detectable limit which indicated that the albumin preparation contained little Hp, $\alpha_1$AG and Tf.

EXAMPLE 3

An albumin preparation was prepared in the same manner as in Example 1 except that QMA-Sepharosil was used in place of QAE-Toyopearl in the anion exchanger treatment step (b).

Experimental Example 2

Recovery rate of albumin and adsorption amount of transferrin (Tf) in the cation exchanger treatment step in the process of preparing albumin preparation in Examples 1 and 2 and Comparative Example are shown in Table 2. The recovery rate of albumin was measured by absorbance at 280 nm. High recovery rate of albumin and high Tf adsorption amount were indicated in the process of the present invention in which polyacrylamide type carrier was used as a cation exchanger. It is clear that the recovery rate of containing proteins is excellent in the process of the present invention.

TABLE 2

| Cation exchanger | Recovery rate of albumin (%) | Adsorption amount of Tf (μg/ml ion exchanger volume) |
| --- | --- | --- |
| SP-Toyopearl (Comparative Example) | 80 | 66 |
| CM-Trisacryl (Example 1) | 95 | 100 or more |
| SP-Trisacryl (Example 2) | 87 | 100 or more |

Experimental Example 3

Polymer content, recovery rate of albumin, degree of coloring and aluminum content of each albumin preparation obtained by the above-mentioned Examples 1 and 3 and Comparative Example were measured. The results are shown in Table 3. As shown in Table 3, highly purified albumin preparation, in which the content of polymers is further reduced and the degree of coloring is low, can be obtained by the process of the present invention. According to the process of the present invention, purification efficiency is excellent due to high recovery rate of albumin.

TABLE 3

|  | Example 1 | Example 3 | Comparative Example |
| --- | --- | --- | --- |
| Content of polymers (wt %) | 0.33 | 0.03 | 0.56 |
| Recovery rate of albumin (%) | 95 | 94 | — |
| Degree of coloring ($A_{405}$/Albumin concentration %) | 0.026 | 0.019 | 0.033 |
| Aluminum content (ppb) | lower than 50 | — | — |

Polyacrylamide type carrier type cation exchanger is used at a cation exchanger treatment step in the process for producing albumin preparation of the present invention. Accordingly, the contaminating proteins, such as transferrin, are further reduced as compared with the conventional method, the polymerization caused by the contaminating proteins can be suppressed and a highly purified albumin preparation can be obtained. The albumin preparation of the present invention is excellent in safety and stability as viruses are inactivated by heat treatment, polymer content is low and content of contaminating proteins is extremely low.

While the invention has been described in detail and with reference to specific examples thereof, it will be apparent to one skilled in the art that various changes and modifications can be made therein without departing from the spirit and scope thereof.

What is claimed is:

1. A process for producing an albumin preparation which comprises the steps of:
   a) treating an aqueous solution containing serum albumin with an anion exchanger;
   b) treating the resultant solution of step (a) with a cation exchanger; and
   c) subjecting the resultant solution of step (b) to heat treatment carried out for a time and at a temperature sufficient to inactivate viruses,
   wherein said cation exchange is a polyacrylamide-type carrier containing cation exchange group.

2. The process for producing an albumin preparation according to claim 1, wherein said polyacrylamide type carrier is poly(N-tris[hydroxymethyl]methylmethacrylamide).

3. The process for producing an albumin preparation according to claim 2, wherein said cation exchanger is carboxymethyl (CM) or sulfopropyl (SP) type poly(N-tris[hydroxymethyl]methylmethacrylamide).

4. The process for producing an albumin preparation according to claim 1, which comprises treating with said cation exchanger at pH 4 to 8.

5. The process for producing an albumin preparation according to claim 4, which comprises treating with said cation exchanger at pH 4.5 to 6.5.

6. The process for producing an albumin preparation according to claim 5, which comprises treating with said cation exchanger at pH 5.0 to 6.0.

7. The process for producing an albumin preparation according to claim 1, wherein said anion exchanger is a strongly basic anion exchanger.

8. The process for producing an albumin preparation according to claim 7, wherein said anion exchanger is quaternary aminoethyl (QAE) type vinyl hydrophilic polymer or quaternary methylammonium (QMA) type porous silica gel.

9. The process for producing an albumin preparation according to claim 1, which comprises treating with said anion exchanger at pH 3 to 6.

10. The process for producing an albumin preparation according to claim 9, which comprises treating with said anion exchanger at pH 4.5 to 5.5.

11. The process for producing an albumin preparation according to claim 10, which comprises treating with said anion exchanger at pH 5.1 to 5.4.

12. The process for producing an albumin preparation according to claim 1, which comprises heat-treating at 50 to 80° C. for 5 to 20 hours.

13. An albumin preparation wherein the content of polymer of albumin is lower than 0.03 wt %.

* * * * *